United States Patent
Wong

(10) Patent No.: US 6,761,696 B1
(45) Date of Patent: Jul. 13, 2004

(54) GUIDE WIRE WITH A NON-RECTANGULAR SHAPING MEMBER

(75) Inventor: Sharon Yan Wong, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/992,838

(22) Filed: Nov. 13, 2001

(51) Int. Cl.[7] .......................... A61B 5/00; A61M 25/00
(52) U.S. Cl. ............................ 600/585; 604/164.13
(58) Field of Search ...................... 600/585, 433, 600/434, 435, 164.13; 604/170.01, 171

(56) References Cited

U.S. PATENT DOCUMENTS

| | | | |
|---|---|---|---|
| 4,538,622 A | | 9/1985 | Samson et al. |
| 4,748,986 A | | 6/1988 | Morrison et al. |
| 4,867,174 A | * | 9/1989 | Skribiski .................... 600/585 |
| 5,061,273 A | | 10/1991 | Yock |
| 5,135,503 A | | 8/1992 | Abrams |
| 5,341,818 A | | 8/1994 | Abrams et al. |
| 5,345,945 A | | 9/1994 | Hodgson et al. |
| 5,636,641 A | | 6/1997 | Fariabi |
| 5,662,585 A | * | 9/1997 | Willis et al. ................ 600/104 |
| 5,673,707 A | * | 10/1997 | Chandrasekaran .......... 600/585 |
| 5,788,654 A | * | 8/1998 | Schwager ................... 600/585 |
| 6,146,338 A | * | 11/2000 | Gardeski et al. ............ 600/585 |
| 6,183,420 B1 | * | 2/2001 | Douk et al. ................. 600/462 |
| 6,464,650 B2 | * | 10/2002 | Jafari et al. ................. 600/585 |
| 2002/0087099 A1 | * | 7/2002 | Nanis et al. ................ 600/585 |

FOREIGN PATENT DOCUMENTS

| | | |
|---|---|---|
| DE | 195 12 047 A | 10/1996 |
| EP | 0 480 427 A | 4/1992 |
| WO | WO 01/26725 A | 4/2001 |

OTHER PUBLICATIONS http://efunda.com/math/areas/rectangle.cfm. Jul. 24, 2003.*

* cited by examiner

*Primary Examiner*—Mary Beth Jones
*Assistant Examiner*—Jonathan Foreman
(74) *Attorney, Agent, or Firm*—Fulwider Patton Lee & Utecht, LLP

(57) ABSTRACT

A guide wire for guiding a medical device within a patient is disclosed. The guide wire includes an elongate core with a flexible body disposed about and secured to a distal core section of the elongate core. A shapeable member extends distally from the distal core section, and the shapeable member preferably includes a nonrectangular, cross-sectional shape including a D-shape, semicircle, a triangle, or the like. In various embodiments, the polygonal shape of the cross-section is defined by a height h and a width b, wherein the moment of inertia of the shapeable member is preferably defined by at least $0.083 \times b \times h^3$.

19 Claims, 2 Drawing Sheets

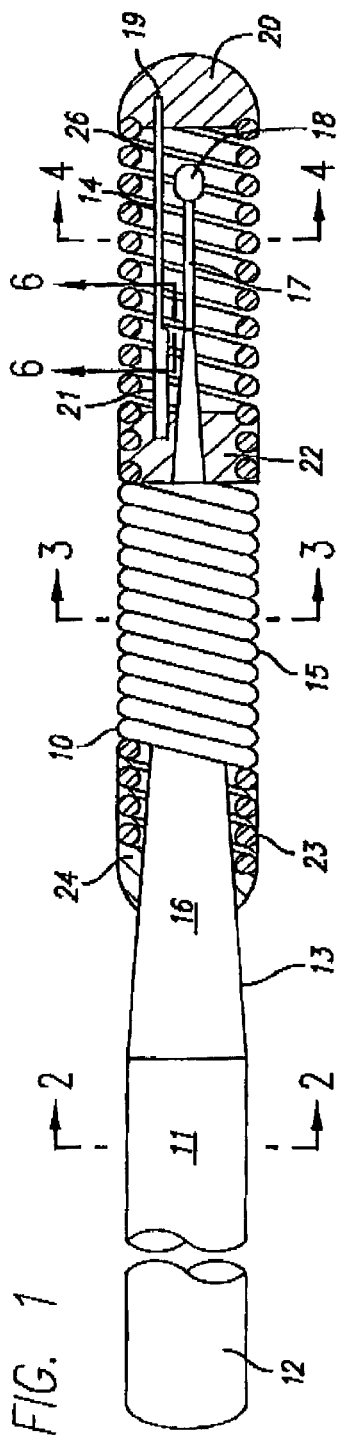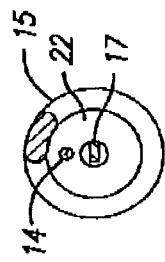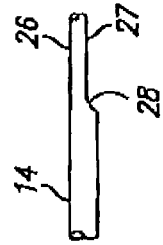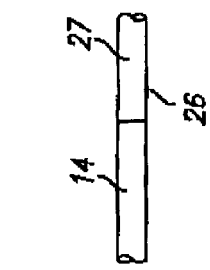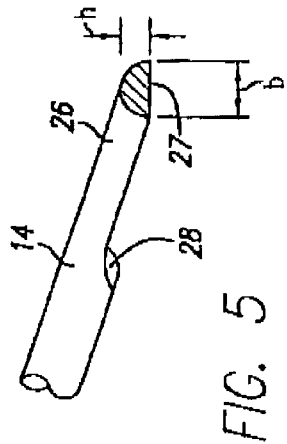

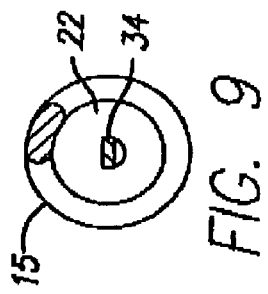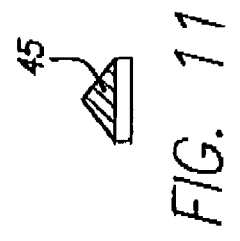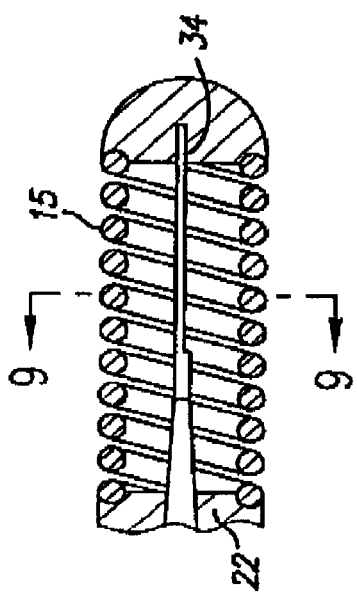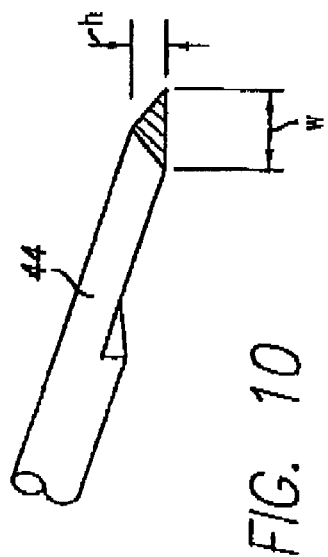

GUIDE WIRE WITH A NON-RECTANGULAR SHAPING MEMBER

BACKGROUND OF THE INVENTION

The present invention relates to the field of advanced medical devices and particularly to intracorporeal devices for performing or aiding in the performance of therapeutic or diagnostic procedures. The intracorporeal devices may be guiding members such as guide wires for advancing intraluminal devices within body lumens. The intracorporeal medical devices include stent delivery catheters, balloon dilatation catheters, atherectomy catheters, electrophysiology catheters and the like.

In a typical percutaneous coronary procedure, a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guide wire is first advanced by itself through the guiding catheter until the distal tip of the guide wire extends beyond the arterial location where the procedure is to be performed. Then a rapid exchange type catheter, such as described in U.S. Pat. No. 5,061,273 (Yock) whose contents are hereby incorporated by reference, is mounted onto the proximal portion of the guide wire which extends out of the proximal end of the guiding catheter which is outside of the patient. The catheter is advanced over the guide wire, while the position of the guide wire is fixed, until the operative element on the rapid exchange type catheter is disposed within the arterial location where the procedure is to be performed. After the procedure is performed, the rapid exchange type catheter may be withdrawn from the patient over the guide wire, or the guide wire may be repositioned within the coronary anatomy for an additional procedure. Of course, the procedure may also be performed with an Over The Wire (OTW) type catheter and is not limited to just Rapid Exchange (RX) type catheters.

A guide wire may also be used in conjunction with the delivery of an intracoronary stent. One method and system involves disposing a compressed or otherwise small diameter stent over an expandable member, such as a balloon, at the distal end of a catheter. The physician advances the catheter through the patient's vascular system over a guide wire until the stent is at the desired location within a blood vessel. The expandable member on the catheter is inflated to expand the stent within the blood vessel. The dilated expandable member is then deflated and the catheter withdrawn, leaving the expanded stent within the blood vessel. Once deployed, the expandable member ensures patency of the blood vessel by holding the passageway open. This latter method and system can be used concurrently with balloon angioplasty or subsequent thereto.

Further details of guide wires and devices associated therewith for various interventional procedures can be found in, for example, U.S. Pat. No. 4,748,986 (Morrison et al.); U.S. Pat. No. 4,538,622 (Samson et al.); U.S. Pat. No. 5,135,503 (Abrams); U.S. Pat. No. 5,341,818 (Abrams et al.); and U.S. Pat. No. 5,345,945 (Hodgson,et al.), whose contents are hereby incorporated by reference.

Conventional guide wires for angioplasty, stent delivery, atherectomy, and other intravascular procedures usually have an elongate core with one or more segments near the distal end thereof that taper distally to smaller cross-sections. A flexible body, such as a helical coil or a tubular body of polymeric material, is typically disposed about and secured to at least part of the distal portion of the core. A shapeable tip, which may be the distal extremity of the core or a separate shapeable ribbon that is secured to the distal extremity of the core, extends through the flexible body and is secured to the distal end of the flexible body by soldering, brazing, or welding; or by use of an adhesive in the case of a polymeric flexible body which forms a rounded distal tip. This rounded, distal or leading tip is highly flexible so that it does not damage or perforate the vessel. The portion behind the distal tip is increasingly stiff to better support a balloon catheter or similar device.

The shapeable member or ribbon of a typical guide wire is a small diameter wire that has been flattened to a relatively constant transverse profile. Flattening of the shapeable member facilitates the shapability of the member. However, a shapeable member having a constant transverse profile or flexibility could be subject to prolapse during use. Prolapse occurs when the shapeable member gets bent back on itself inside a constrained lumen, and is difficult to straighten out with only proximal manipulation.

SUMMARY OF THE INVENTION

The present invention is generally directed to a medical device such as a guiding member for performing or aiding in the performance of a therapeutic or diagnostic procedure. In various exemplary embodiments, the present invention is directed to a guide wire or similar guiding member for the introduction and advancement of a medical device into a patient for the performance of a therapeutic or diagnostic procedure.

A guiding member embodying features of the present invention generally has a shapeable member, which extends from a distal core section and has a distal portion extending beyond the distal core section with a non-rectangular cross-sectional shape defined by width b and a height h. In one embodiment, the present invention guide wire includes a moment of inertia having a moment of inertia defined by $0.083 \times b \times h^3$. Preferably, the value for the moment of inertia is defined by at least $0.1 \times b \times h^3$.

The guiding member may have an elongate core with a proximal core section and a distal core section, and a flexible body disposed about and secured to at least a portion of the distal core section. The shapeable member has a distal end that is optionally secured to the distal end of the flexible body that terminates in a rounded tip. The portion of the shapeable member having the desired moment of inertia preferably has a cross-sectional shape including a non-rectangular shape, a D-shape, a triangular shape, and the like. Other non-rectangular shapes known in the art having the desired moment of inertia may also be employed.

The shapeable member may be separately formed and then joined to the distal core section in a suitable manner, or it may be formed out of a distal extremity of the core. If separately formed, the elongated shapeable member may be formed as a shaping ribbon that is mounted or attached in a suitable manner to the distal extremity of the distal core section through welding, brazing, soldering, adhesive bonding, mechanical connections, and other known mounting processes. In addition, the discrete shapeable member may by formed from round or flattened wire that is coined, rolled, or otherwise plastically deformed to a desired shape with preferably a non-rectangular cross-sectional shape.

A flexible body may be disposed about the shapeable member, preferably along its entire length and may take the form of a helical coil, polymer jacket, or the like. The distal end of the flexible body is attached to the distal end of the shapeable member and an intermediate portion of the flexible body is preferably secured to the distal core section proximal to the shapeable member. The intermediate portion of the flexible body can optionally be secured to the distal core section including the proximal end of the shapeable member.

The non-rectangular, transverse shape of the elongated shapeable member on the distal part of the guide wire changes the moment of inertia of the shapeable member as compared to one having a rectangular transverse cross-section with the same width and height, thus making the shapeable member with a non-rectangular transverse cross-section more or less flexible, depending on the non-rectangular transverse shape chosen. Furthermore, the non-rectangular transverse shape may provide for a larger or smaller profile for the shapeable member with the same strength characteristics as a shapeable member with a rectangular transverse shape.

In various embodiments, the length of the shapeable member is about, for example, 0.5 cm to about 12 cm, and preferably about 1 cm to about 10 cm. At least 50%, and preferably at least 75%, of the length of the shapeable member is optionally tapered. The taper may be straight or curved, and divergent or convergent. As to the latter, for example, the shapeable member preferably has two pairs of opposing faces that are essentially the mirror image of each other. In one embodiment, the pair of opposing faces converge toward each other while in another embodiment the pair of opposing faces diverge from each other. There may be more than one taper resulting in a shapeable member that is thicker in the middle or thinner in the middle.

Lastly, the geometry of the shapeable member may be modeled mathematically. The specific transverse shapes may be selected in keeping with the principles of the invention to achieve optimum performance for specific usage requirements. These and other advantages of the invention will become more apparent from the following detailed description of the invention when taken in conjunction with the accompanying exemplary drawings.

BRIEF DESCRIPTION OF THE DRAWINGS

FIG. 1 is a side elevational view, shown partially in cross-section, of a guide wire embodying features of the present invention.

FIG. 2 is a cross-sectional view of the guide wire shown in FIG. 1 taken along line 2—2.

FIG. 3 is a cross-sectional view of the guide wire shown in FIG. 1 taken along line 3—3.

FIG. 4 is a cross-sectional view of the guide wire shown in FIG. 1 taken along line 4—4.

FIG. 5 is a partial perspective view of the shapeable member shown in FIG. 1.

FIG. 6 is a partial plan view of the shapeable member shown in FIG. 1 taken along the line 6—6.

FIG. 7 is a partial, side elevational view of the shapeable member shown in FIG. 1.

FIG. 8 is a partial, longitudinal cross-sectional view of a guide wire embodying alternative features of the invention in which the shapeable member is a contiguous extension of the core.

FIG. 9 is a cross-sectional view of the guide wire shown in FIG. 8 taken along the line 9—9.

FIG. 10 is a partial perspective view of an alternative embodiment shapeable member.

FIG. 11 is an end view of the shapeable member shown in FIG. 10.

DETAILED DESCRIPTION OF THE PREFERRED EMBODIMENTS

The present invention in an exemplary embodiment is directed to a guide wire having a unique shaping ribbon, and specifically, a shapeable member with a nonrectangular, transverse cross-sectional shape. FIGS. 1–7 illustrate one embodiment of the present invention guide wire 10 that includes an elongated core 11, with a proximal core section 12, a distal core section 13, the shapeable member 14, and a flexible body 15 which in this embodiment is a helical coil. Preferably, the flexible body 15 is disposed about and secured to the distal core section 13. The distal core section 13 has an optional tapered core segment 16 and an optional flexible core segment 17 which is distally contiguous to the tapered core segment 16. At the very distal end of the flexible core segment 17 is a rounded distal extremity 18. Of course, the rounded distal extremity 18 may be of other shapes and sizes, can be flattened, or omitted altogether. In fact, in an alternative embodiment core-to-tip design, the core segment 17 extends continuously to engage a rounded tip 20 at the very distal end of the guide wire 10.

FIGS. 2–4 are cross-sectional views of the guide wire 10 taken along lines 2—2, 3—3, and 4—4 respectively. At a proximal end of the guide wire 10, FIG. 2 shows core 11 and optional lubricious coating 25. The lubricious coating 25 covers the core 11 in part or fully, and serves to ease movement of the guide wire 10. At an intermediate position of the guide wire 10, FIG. 3 shows tapered core segment 16 and the overlying flexibly body 15. At the distal end of the guide wire 10, FIG. 4 depicts the flexible body 15 surrounding shapeable member 14 and flexible core segment 17.

The distal end 19 of the elongated shapeable member 14 is secured to the rounded tip 20 as shown in FIG. 1 by soldering, welding, adhesive bonding, or through a mechanical interlocking engagement known in the art. At the opposite end, the proximal end 21 of the shapeable member 14 is joined to the distal core section 13 by a weld or solder bead 22. Through the same mechanism, the solder or weld bead 22 can also secure an intermediate portion of the flexible body 15 to the distal core section 13. The proximal end of the flexible body 15 is attached to the distal core section 13 by use of a bead 24 of solder or weld. Other processes known in the art aside from soldering or welding for joining the aforementioned sundry parts together are also contemplated.

As shown in greater detail in FIG. 5, the shapeable member 14 has preferably a semi-circular or D-shaped distal portion 26 with an edge from an end view that translates into a flat surface 27 in three dimensions. FIG. 6 is a plan view and FIG. 7 is a side elevational view of the semi-circular shaped distal portion 26. As best seen in FIG. 7, the flat surface 27 has an optional fillet 28 at its base where it transitions from a larger cross-section to a smaller cross-section to reduce stress accumulation. The fillet 28 may be replaced with a taper, slope, step, or the like.

The semi-circular, cross-sectional shape of distal portion 26 is defined by a width b and a height h. Associated with the cross-sectional D-shape is its area moment of inertia. It has been determined that the semi-circular distal portion 26 has a moment of inertia defined by the product of $0.14 \times b \times h^3$. This equation is derived from the equation $(8b \times h^3)/9\pi$, where b is the maximum width dimension and h is the maximum height dimension. In an exemplary embodiment of the present invention, the moment of inertia for a constant, non-rectangular shapeable member 14 is defined by at least $0.083 \times b \times h^3$, and preferably has a value for the moment of inertia defined by at least $0.1 \times b \times h^3$. In various embodiments, the values are defined as follows: 0.0001 inch$\leq b \leq$0.035 inch, and 0.0001 inch$\leq h \leq$0.035 inch; and preferably, 0.0001 inch$\leq b \leq$0.012 inch, and 0.0001 inch$\leq h \leq$0.012 inch.

For a given width b and height h, the present invention D-shape shapeable member 14 can be made to be stiffer or floppier than a shapeable member having a rectangular cross-section of the same width b and height h. To do this, a D-shaped member could be made to be stiffer or floppier as compared to a rectangular cross-sectional member with the same width and height by adjusting the length of that member (i.e., adjusting the third dimension). Since the moment of inertia of a D-shaped member is larger than that of a rectangular member, if the length and material remained constant, then the shapeable member would be stiffer. However, that is not to say that the D-shaped member could not be made floppier than its rectangular counterpart. The length could be made longer for a greater moment arm in order to counteract the increased stiffness from the moment of inertia contribution.

Alternatively, a specific area at a location relative to the centroid of the entire cross-sectional area is increased or decreased. This obviously changes the shape of the cross-section. As a result, the bending moment in that direction is increased or decreased accordingly. For instance, by increasing the area above the centroid of the semi-circular cross-section of the distal portion 26, the rigidity or resistance to bending of the distal portion 26 in that direction is increased conversely, decreasing that area decreases the bending moment and rigidity in that direction, making for a floppier shapeable member.

In FIG. 1, the shapeable member 14 is illustrated as being a structure discrete from the distal core section 13. Of course, in various other embodiments, the shapeable member may be formed as an integral part of the distal core section 13. For example, FIGS. 8 and 9, which has reference numbers essentially the same as those shown in FIG. 1 except as otherwise noted, depicts the shaping member 34 as being formed integrally with the distal core section 13.

In an alternative embodiment shown in FIGS. 10 and 11, the shapeable member has a distal portion 44 having a triangular cross-section 45. This is shown in the perspective view in FIG. 10 and in a cross-sectional view in FIG. 11. As best seen in FIG. 10, the triangular cross-section has a base or width w and a height h. As in the embodiment shown in FIG. 5, the base is formed by a flat face which transitions from a larger cross-section proximal to the distal portion 44. The transition may be stepped as illustrated, or may be made with a fillet 28 as seen in FIG. 5. Furthermore, the triangular cross-section 45 is shown as an isosceles triangle, but scalene and equilateral triangles are contemplated. In fact, any non-rectangular polygon may be used, as well as ovoids and the like.

The semi-circular shaped distal portion 26 of the shapeable member 14, 34 has a constant dimension along the length thereof. On the other hand, the moment of inertia of the semi-circular shaped distal portion 26 may by changed progressively by optionally tapering the shapeable member 14, 34. Moving in a distal direction along the length of the shapeable member 14, 34, the taper can converge or diverge. As best seen in the side elevational view of FIG. 8, the shapeable member 34 has a divergent taper such that the distal location thereof is fatter than a proximal location thereof. Whether converging or diverging, the taper is accomplished by increasing or decreasing either width b or height h, or both dimensions simultaneously.

If the D-shaped cross-section was produced from a constant diameter cross-section, as in the case of mechanical flattening of a round wire to form the D-shape, then the cross-sectional area of the D-shaped member remains the same even if tapered due to conservation of area. And assuming that the D-shape was formed from a round wire, then the cross-sectional area remains the same. Hence, it is the ratio of the dimensions that increases or decreases the moment of inertia and thus the stiffness of the shapeable member 14, 34.

On the other hand, if the D-shape was formed from a non-constant diameter round wire (i.e., from a tapered wire), then the smaller the cross-sectional area, the lower the moment of inertia, and the less stiff the shapeable member is. It is in that situation where the cross-sectional area can change at different locations of the shapeable member.

As discussed above, in an alternative embodiment, increasing or decreasing one dimension b or h relative to the other dimension creates increased or decreased bending moments in that direction, respectively. Hence, stiffness or rigidity of the shapeable member 14, 34 can be controlled in various directions.

The configuration of the shapeable member of the present invention may be generated by a centerless grinder. Tapers or flat faces may also be formed by other means such as by etching or lasers. The distal core section 13 may also have more than one taper 16, such as described in U.S. patent application Ser. No. 08/868,764, filed Jun. 4, 1997 by inventors Cornish, et al., entitled STEERABLE GUIDEWIRE WITH ENHANCED DISTAL SUPPORT, which is hereby incorporated by reference.

In various embodiments, the length of the shapeable member is about, for example, 0.5 cm to about 12 cm, and preferably about 1 cm to about 10 cm. At least 50%, and preferably at least 75%, of the length of the shapeable member is optionally tapered. Alternatively, if the taper has a length l, then the length of the taper is defined by 0.25 cm$\leq l \leq$3 cm.

In various embodiments of the present invention guide wire, the core 11 may be formed from stainless steel, NiTi alloys, or combinations thereof such as described in U.S. Pat. No. 5,341,818 (Abrams et al), which is incorporated herein by reference. Other materials such as the high strength alloys described in U.S. Pat. No. 5,636,641 (Fariabi), entitled HIGH STRENGTH MEMBER FOR INTRACORPOREAL USE, which is incorporated herein by reference, may also be used.

The optional lubricious coating 25 on the core 11 may be a fluoropolymer such as TEFLON available from DuPont. It extends preferably at least the length of the proximal core section 12. The distal section 13 is also optionally provided with a lubricious coating known in the art as a MICRO-GLIDE™ coating. Hydrophilic coatings may also be employed on both the proximal and distal portions of the guide wire.

The overall length and diameter of guide wire 10 may be varied to suit the particular procedures in which it is to be used and is dependent on the materials from which it is constructed. Generally, the length of the guide wire 10 ranges from about 65 cm to about 320 cm, and more typically ranging from about 160 cm to about 200 cm.

Commercially available guide wires for coronary anatomy typically have lengths of about 175 cm or about 190 cm. Guide wire diameters generally range from about 0.008 inch to about 0.035 inch (0.2 to 0.9 mm), and more typically range from about 0.01 inch to about 0.018 inch (0.25 to 0.55 mm). Commercially available guide wires for coronary use typically have diameters of about 0.01, 0.012 and 0.014 inch (0.25, 0.3 and 0.036 mm, respectively).

In various embodiments, the helical wire coil from which the flexible body 15 is made generally has a transverse diameter of about 0.001 to about 0.004 inch (0.025–0.1 mm), and preferably about 0.002 to about 0.003 inch (0.05-0.008 mm). Multiple turns of the distal portion of flexible body 15 may be expanded to provide additional flexibility. The flexible body 15 may have a diameter or transverse dimension that is about the same as the proximal core section 12. The flexible body 15 may have a length of about 2 cm to about 40 cm or more, and preferably about 2 cm to about 10 cm in length. Furthermore, the flexible body 15 may at least in part be formed of a suitable radiopaque material such as platinum, palladium, or alloys thereof, or formed of other materials such as stainless steel and coated with a radiopaque material such as gold. In addition, the flexible body 15 may instead of a helical coil be a sleeve formed from a polymeric material such as polyamide, polyethylene, polyurethane, TFE, PTFE, EPTFE and other similar materials.

To the extent not otherwise described herein, the materials and methods of construction and the dimensions of conventional intracorporeal devices such as intravascular guide wires may be employed with a device embodying features of the present invention. Moreover, features disclosed with one embodiment may be employed with other described embodiments.

What is claimed is:

1. A guiding member for incorporeal procedures, comprising:
    an elongate core having a proximal core section and a distal core section;
    a flexible body that is disposed about and secured to at least a portion of the distal core section; and
    a shapeable member extending from the distal core section, wherein the shapeable member includes a cross-sectional area with a shape including a distal edge having a height h and a width b, and wherein an area moment of inertia relative to a centroid of the cross-sectional area of the shapeable member is at least $0.1 \times b \times h^3$.

2. The guiding member of claim 1, wherein 0.0001 inch $\leq$ b $\leq$ 0.035 inch, and 0.0001 inch $\leq$ h $\leq$ 0.035 inch.

3. The guiding member of claim 1, wherein 0.0001 inch $\leq$ b $\leq$ 0.012 inch, and 0.0001 inch $\leq$ h $\leq$ 0.012 inch.

4. The guiding member of claim 1, wherein the shapeable member includes at least one taper.

5. The guiding member of claim 4, wherein the taper has a length l such that 0.25 cm $\leq$ l $\leq$ 3 cm.

6. The guiding member of claim 4, wherein the taper converges distally.

7. The guiding member of claim 4, wherein the taper diverges distally.

8. The guiding member of claim 1, wherein 50% to 75 % of a length of the shapeable member includes a taper.

9. The guiding member of claim 1, wherein the cross-sectional shape includes a D-shape.

10. The guiding member of claim 1, wherein the cross-sectional shape includes a non-rectangular polygon.

11. The guiding member of claim 1, wherein the shapeable member is attached to the distal core section.

12. The guiding member of claim 1, wherein the shapeable member includes a triangular cross-sectional shape.

13. The guiding member of claim 1, wherein the shapeable member includes a semi-circular cross-sectional shape.

14. A guiding member as defined in claim 1, wherein said shapeable member further comprises a larger cross-sectional portion, and a fillet defines a transition between said larger-cross sectional portion and said cross-sectional shape.

15. A guiding member as defined in claim 1, wherein said shapeable member further comprises a larger cross-sectional portion, and a single fillet defines a transition between said larger-cross sectional portion and said cross-sectional shape.

16. A guiding member as defined in claim 1, wherein said shapeable member further comprises a larger cross-sectional portion, and wherein one of a group constituting a taper, a slope, and a step defines a transition between said larger-cross sectional portion and said cross-sectional shape.

17. A method for providing a guide wire for intracorporeal procedures, comprising:
    providing an elongate core having a proximal core section and a distal core section;
    providing a flexible body;
    disposing the flexible body over at least a portion of the distal core section; and
    providing a shapeable member extending distally from the distal core section having a transverse cross-sectional shape including a distal edge having a width b and a height h, wherein the shapeable member includes an area moment of inertia of the cross-sectional shape relative to a centroid thereof of at least $0.1 \times b \times h^3$.

18. The method of claim 17, wherein the method includes connecting the shapeable member to the distal core section through a process selected from the group consisting of soldering, welding, adhesive bonding, or mechanically fastening.

19. The method of claim 17, wherein the method includes extending the shapeable member from the distal core section through a process selected from the group consisting of rolling, coining, stamping, extruding, drawing, or swaging.

* * * * *

UNITED STATES PATENT AND TRADEMARK OFFICE
CERTIFICATE OF CORRECTION

PATENT NO. : 6,761,696 B1  
DATED : July 13, 2004  
INVENTOR(S) : Sharon Yan Wong It is certified that error appears in the above-identified patent and that said Letters Patent is hereby corrected as shown below:

Column 7,  
Line 43, delete "including a distal edge".  
Line 44, delete "and".  
Line 46, after "0.1xbxh$^3$" add --; and wherein the cross-sectional area extends to a distal edge of the shapeable member --.

Column 8,  
Line 41, delete "including a distal edge".  
Line 44, after "0.1xbxh$^3$" add --; and wherein the cross-sectional area extends to a distal edge of the shapeable member --.

Signed and Sealed this

Fifteenth Day of February, 2005

JON W. DUDAS  
*Director of the United States Patent and Trademark Office*